US00PP25382P2

(12) United States Plant Patent
Verduin

(10) Patent No.: US PP25,382 P2
(45) Date of Patent: Mar. 24, 2015

(54) ***ASTILBE* PLANT NAMED 'HONKY TONK'**

(50) Latin Name: ***Astilbe* hybrid**
Varietal Denomination: Honky Tonk

(71) Applicant: Henricus Gijsbertus Johannes Verduin, Heemskerk (NL)

(72) Inventor: Henricus Gijsbertus Johannes Verduin, Heemskerk (NL)

( * ) Notice: Subject to any disclaimer, the term of this patent is extended or adjusted under 35 U.S.C. 154(b) by 90 days.

(21) Appl. No.: 13/815,453

(22) Filed: Mar. 4, 2013

(51) Int. Cl.
*A01H 5/00* (2006.01)

(52) U.S. Cl.
USPC ..... Plt./407

(58) Field of Classification Search
USPC ..... Plt./407
See application file for complete search history.

(56) References Cited

PUBLICATIONS

PLUTO Plant Variety Database search for Honky Tonk. p. 1.*

* cited by examiner

*Primary Examiner* — Annette Para
(74) *Attorney, Agent, or Firm* — Penny J. Aguirre

(57) ABSTRACT

A new cultivar of *Astilbe* named 'Honky Tonk' that is characterized by its rich clear pink flowers, its numerous flowering stems, its sturdy and upright flowering stems, its growth medium green foliage, and its suitability for use as a cut flower.

2 Drawing Sheets

Botanical classification: *Astilbe* hybrid.
Varietal denomination: 'Honky Tonk'.

BACKGROUND OF THE INVENTION

The present invention relates to a new and distinct cultivar of *Astilbe* of hybrid origin and will be referred to hereafter by its cultivar name, 'Honky Tonk'. 'Honky Tonk' represents a new *Astilbe*, an herbaceous perennial grown for landscape and cut flower use.

The Inventor discovered the new cultivar, 'Honky Tonk', as naturally occurring whole plant mutation (spontaneous seedling) in trial garden at his nursery in Heemskerk, The Netherlands in July of 2005. The parentage is therefore unknown.

Asexual propagation of the new cultivar was first accomplished by division by the Inventor in Heemskerk, The Netherlands in January of 2006. Asexual propagation by division has determined that the characteristics of the new cultivar are stable and are reproduced true to type in successive generations.

SUMMARY OF THE INVENTION

The following traits have been repeatedly observed and represent the characteristics of the new cultivar as observed in trials in Heemskerk, The Netherlands. These characteristics in combination distinguish 'Honky Tonk' as a unique cultivar of *Astilbe*.

1. 'Honky Tonk' exhibits rich, clear pink flowers.
2. 'Honky Tonk' produces numerous flowering stems.
3. 'Honky Tonk' exhibits sturdy, upright flowering stems.
4. 'Honky Tonk' exhibits medium green foliage.
5. 'Honky Tonk' is well suited for production of cut flowers.

'Honky Tonk' can be most closely compared to the cultivars: 'Rheinland' (not patented), 'Cotton Candy' (not patented), and 'Touch of Pink' (U.S. Plant Pat. No. 11,950). 'Rheinland' differs from 'Honky Tonk' in having inflorescences that are more rose-pink in color and in having a less vigorous growth habit. 'Cotton Candy' differs from 'Honky Tonk' in having inflorescences that are more rose-pink in color, in being smaller in stature, and in having a more mounded plant habit. 'Touch of Pink' differs from 'Honky Tonk' in being lighter pink in color and in being smaller in stature.

BRIEF DESCRIPTION OF THE PHOTOGRAPHS

The plants in the photographs depict a 14 month-old plant of 'Honky Tonk' as grown in a greenhouse in a 3-liter container in Heemskerk, The Netherlands.

Figure 1:
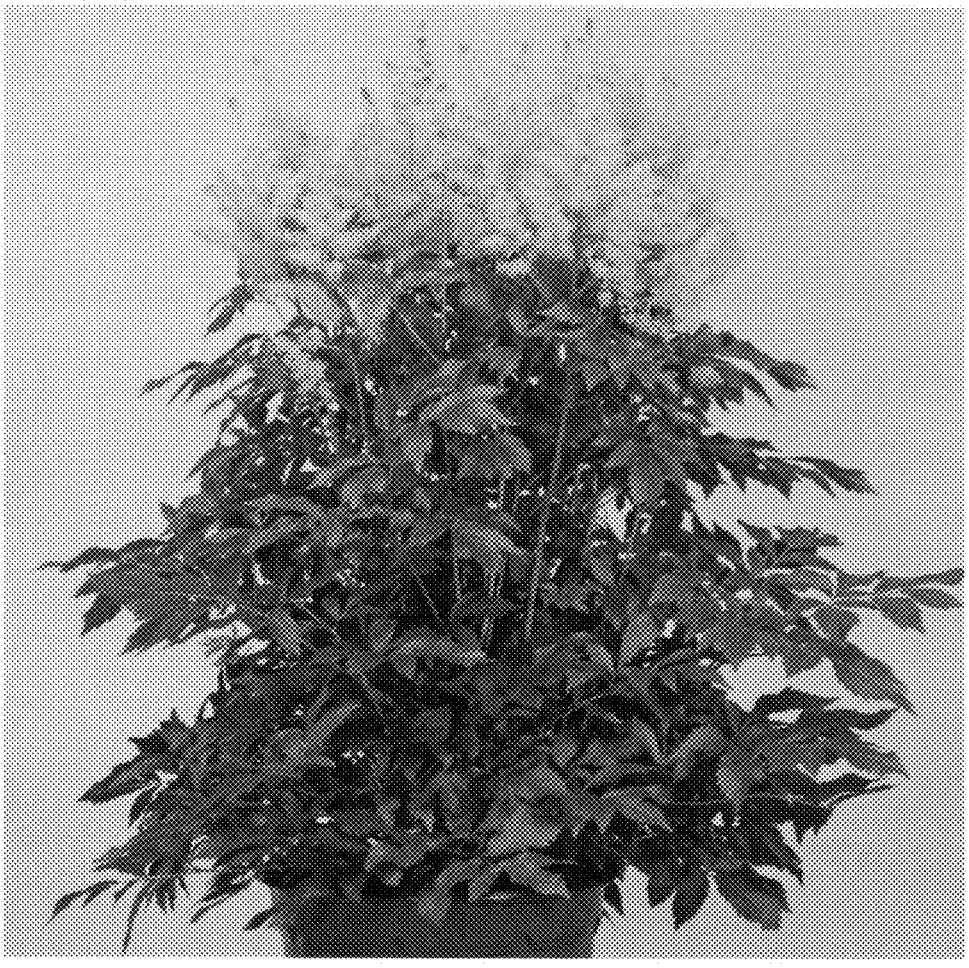

The photograph in FIG. 1 provides a side view of the new 'Honky Tonk' in bloom.

Figure 2:
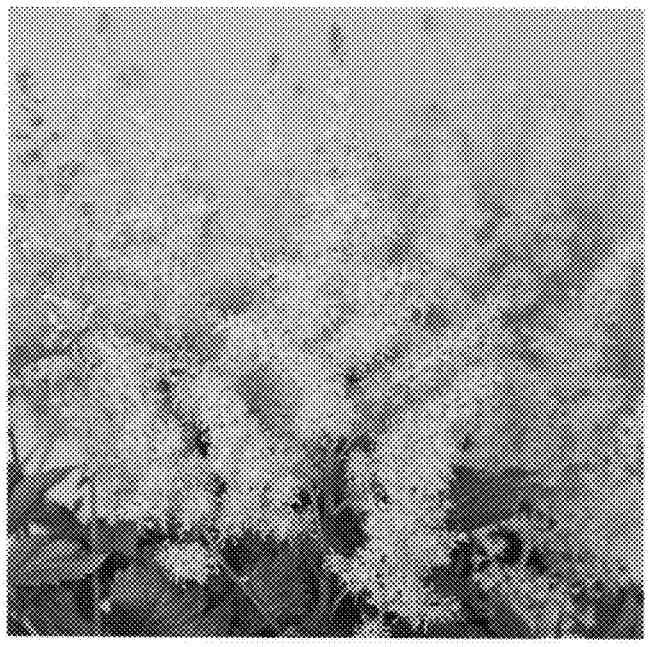

The photograph in FIG. 2 provides a close-up view of an inflorescence of 'Honky Tonk'.

Figure 3:
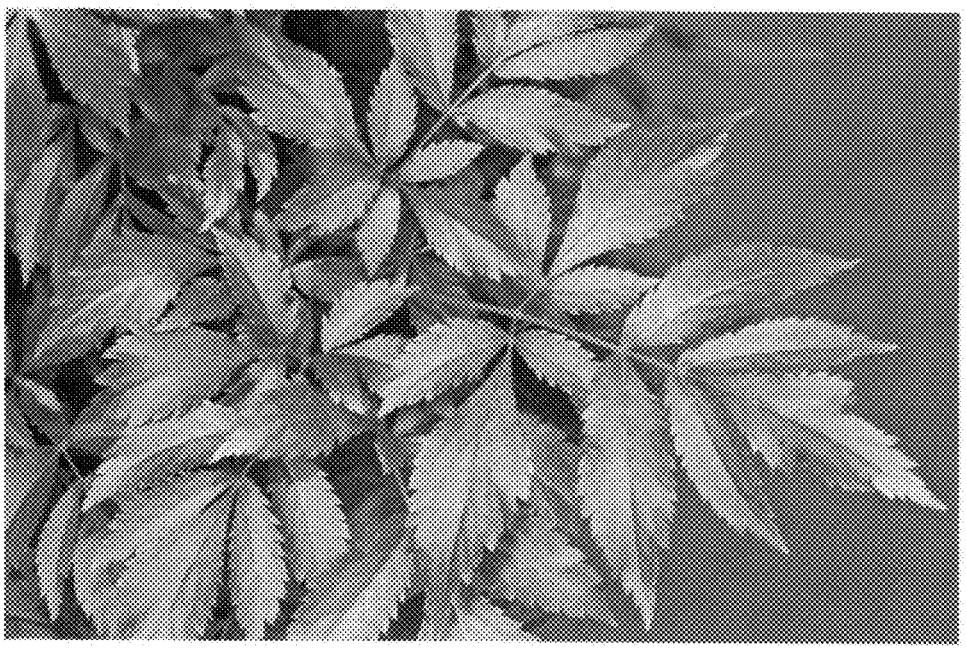

The photograph in FIG. 3 provides a close-up the foliage of 'Honky Tonk'.

The colors in the photographs are as close as possible with the digital photography and printing techniques utilized and the color codes in the detailed botanical description accurately describe the colors of the new *Astilbe*.

DETAILED BOTANICAL DESCRIPTION

The following is a detailed description of 14 month-old plants as grown in a greenhouse in 3-liter containers in Heemskerk, The Netherlands. Plants were grown under average day temperatures ranging from 15° to 20° C. and average night temperatures ranging from 12° to 16° C. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period.*—Early summer to late summer in The Netherlands.

*Plant type.*—Herbaceous perennial.

*Plant habit.*—Clump-forming, broadly upright with blooming stems held erect.

*Height and spread.*—45 to 55 cm in height and 50 to 60 cm in spread in the landscape.

*Cold hardiness.*—At least to U.S.D.A. Zone 5.

*Diseases and pests.*—Has been observed to have healthy foliage, no particular disease or pest resisitance or susceptibility has been observed.

*Propagation.*—Division.

*Growth rate.*—Moderate.

Stem description (flowering stems):

*Stem color.*—144A, and 144B near base.

*Stem shape.*—Round.

*Stem size.*—Average of 29 cm in length and 3 mm in diameter.

*Stem quantity.*—Average of 19 main stems.

*Stem surface.*—Moderately glossy, bases of stems moderately covered with very short hairs, average of 1 mm in length and N170B in color.

*Stem aspect.*—Very strong, held upright.

*Branching habit.*—No lateral branches, stems grow from the base.

Foliage description:

*Leaf division.*—Compound.

*Leaf attachment.*—Petiolate.

*Leaf arrangement.*—Alternate.

*Leaf shape.*—Biternate.

*Leaf number.*—Average of 3 per lateral branch.

*Internode length.*—Average of 9.4 cm.

*Leaf size.*—Average of 15.7 cm in length and 16.1 cm in width.

*Leaf color.*—Young foliage upper surface; 143B to 143C, young foliage lower surface; 143C, mature foliage upper surface; N137A, mature foliage lower surface; 138A.

*Leaflet quantity.*—Average of 27 per leaf.

*Leaflet shape.*—Elliptic.

*Leaflet base.*—Long acuminate.

*Leaflet apex.*—Apiculate.

*Leaflet venation.*—Pinnate, color of upper surface; 138B, color of lower surface; 138B to 138C.

*Leaflet margins.*—Biserrate.

*Leaflet size.*—Average of 4.4 cm in length and 1.6 cm in width.

*Leaflet surface.*—Both surfaces moderately glossy, slightly rough to the touch due to being sparsely covered with short strigose hairs, average length 0.5 mm, 157D in color.

*Petioles.*—Leaf; average of 10.3 cm in length, 1.5 mm in diameter and 144B in color, glabrous surface, petiolules on leaflet; average of 1.4 cm in length, 1 mm in diameter and 144B in color, glabrous surface.

*Stipules.*—Both sides of the leaf base have a dry leafy stipule, ovate in shape, average of 5 mm in length, 4 mm in width and N199D in color.

Flower description:

*Inflorescence type.*—Numerous single rotate shaped flowers arranged on pyramidal panicles.

*Inflorescence aspect.*—Upright and held above foliage.

*Inflorescence size.*—Average of 15.9 cm in height and 10.4 cm in width.

*Flower fragrance.*—Moderately strong, sweet and pleasant fragrance.

*Flower quantity.*—Average of 1,000 per inflorescence.

*Flower lastingness.*—Average of 10 days.

*Flower lastingness as a cut flower.*—Average of one week in water.

*Flower buds.*—Broadly elliptic in shape, average of 2 mm in length and 1.5 mm in diameter, color; 67A, base 145C.

*Flower aspect.*—Upright, outward, and drooping.

*Flower shape.*—Rotate.

*Flower size.*—About 5 mm in depth and 7 mm in diameter.

*Petals.*—Average of 5, un-fused, oblanceolate in shape, margin is entire, apex is broadly acute, average of 4 mm in length and 1 mm in width, upper and lower surface when opening; 68B, upper and lower surface when fully open; 73C, all fading to 73D.

*Calyx.*—Campanulate, average of 2 mm in length and 3 mm in diameter.

*Sepals.*—5, ovate in shape, margin is entire, apex is acute, base is ovate and fused, surface is smooth and dull, color of upper and lower surface when immature; 145C, color of upper and lower surface when mature; 150D, about 0.75 mm in width and 2 mm in length.

*Peduncles.*—Average of 15.5 cm in length and 1.5 mm in diameter, held at 0° (straight upright), peduncles of secondary racemes; held at an average angle of 40°, strong, color is 144B, glabrous surface.

*Pedicels.*—About 1.5 mm in length and 0.5 mm in width, held at an average angle of 45°, 150D in color, glabrous surface.

Reproductive organs:

*Gynoecium.*—2 Pistils, about 1 mm in length, stigma is club-shaped and 53D in color, style is about 0.8 mm in length and 65C in color, ovary is 65D in color.

*Androcoecium.*—About 10 stamens, anthers are ovate in shape, basifixed, about 0.2 mm in length and 63C in color, filaments are about 2 mm in length and 62B in color, pollen is very low in quantity and N155A in color.

*Seed and fruit.*—No seeds or fruit have been detected to date.

It is claimed:

1. A new and distinct cultivar of *Astilbe* plant named 'Honky Tonk' as herein illustrated and described.

* * * * *